United States Patent [19]

Bourland et al.

[11] Patent Number: 5,010,772
[45] Date of Patent: Apr. 30, 1991

[54] PRESSURE MAPPING SYSTEM WITH CAPACITIVE MEASURING PAD

[75] Inventors: Joe D. Bourland; Charles F. Barbs; Leslie A. Geddes; Willis A. Tacker, Jr.; George P. Graber, all of W. Lafayette, Ind.

[73] Assignee: Purdue Research Foundation, West Lafayette, Ind.

[21] Appl. No.: 347,921

[22] Filed: May 5, 1989

Related U.S. Application Data

[63] Continuation-in-part of Ser. No. 850,518, Apr. 11, 1986, Pat. No. 4,827,763.

[51] Int. Cl.$^5$ ............................ A61B 5/10; G01L 5/00; G01L 1/14
[52] U.S. Cl. ..................................... 73/862.04; 73/172
[58] Field of Search ............................... 73/172, 862.04

[56] References Cited

U.S. PATENT DOCUMENTS

| | | |
|---|---|---|
| 2,378,039 | 6/1945 | Schenker . |
| 2,644,332 | 7/1953 | Ulrich . |
| 3,118,133 | 1/1964 | Meeker et al. . |
| 3,818,756 | 6/1974 | Barron et al. . |
| 3,394,437 | 7/1975 | Hagy et al. . |
| 3,926,177 | 12/1975 | Hardway Jr. et al. . |
| 4,030,347 | 6/1977 | Norris et al. . |
| 4,033,332 | 7/1977 | Hardway Jr. et al. . |
| 4,102,422 | 7/1978 | Christiansson . |
| 4,134,063 | 1/1979 | Nicol et al. . |
| 4,136,682 | 1/1979 | Pedotti . |
| 4,144,877 | 3/1979 | Frei et al. . |
| 4,250,894 | 2/1981 | Frei et al. . |
| 4,266,263 | 5/1981 | Haberl et al. . |
| 4,267,728 | 5/1981 | Manley et al. . |
| 4,320,766 | 3/1982 | Alihanka et al. . |
| 4,353,056 | 10/1982 | Tsikos . |
| 4,367,385 | 1/1983 | Frame . |
| 4,381,788 | 5/1983 | Douglas . |
| 4,402,326 | 9/1983 | Okano et al. . |
| 4,437,138 | 3/1984 | Nicol . |
| 4,526,043 | 7/1985 | Boie et al. . |
| 4,600,016 | 7/1986 | Boyd et al. . |
| 4,644,801 | 2/1987 | Kustanovich . |
| 4,827,763 | 5/1989 | Bourland et al. ..................... 73/172 |

FOREIGN PATENT DOCUMENTS

| | | |
|---|---|---|
| 2653556 | 6/1977 | Fed. Rep. of Germany . |
| 54-153057 | 12/1979 | Japan . |
| 0206423 | 9/1987 | Japan .............................. 73/862.04 |
| 2071852 | 9/1981 | United Kingdom . |

OTHER PUBLICATIONS

Katz et al.–"A MOS LSI Capacitive Keyboard Interface Chip", 1978 IEEE International Solid-State Circuits Conference, Digest of Technical Paper, pp. 202–203, Feb. 1978.

*Primary Examiner*—Charles A. Ruehl
*Attorney, Agent, or Firm*—Burns, Doane, Swecker & Mathis

[57] ABSTRACT

A capacitive measuring pad is constructed of transverse conductive strips separated by a compressible insulator to form a matrix of pressure sensitive capacitive nodes. The nodes are repetitively scanned in sequence by a microcomputer to measure their respective capacitances, from which measurements a pressure map is then derived. The resulting pressure map may be displayed on a color graphics monitor with different colors representing diffrent pressures. Node capacitance is found by measuring the response of the mode to a driving signal of a known voltage. This measurement is accomplished by connecting one of the node's transverse conductive strips to the driving source and the node's other conductive strips to a sense amplifier. In order to isolate the node of interest from the influence of surrounding nodes, all of the conductive strips except the two intersecting the selected node are connected to ground. Furthermore, the input impedance to ground of the sense amplifier is made negligibly small with respect to the other system impedance. In this way, only the conductive strip connected to the driving source has a voltage impressed on it, and the conductive strips of all other nodes in the system are maintained at ground potential, thus allowing an accurate measurement of the one capacitance.

21 Claims, 9 Drawing Sheets

PRESSURE MAPPING SYSTEM WITH CAPACITIVE MEASURING PAD

The present application is a continuation-in-part application of parent application U.S. Ser. No. 850,518, filed Apr. 11, 1986 and allowed on May 9, 1989 as U.S. Pat. No. 4,827,763.

BACKGROUND OF THE INVENTION

The present invention is directed to a system for detecting and measuring pressure distribution, and more particularly to a system which employs a pad to provide a quantitative indication of pressure distribution on a surface.

Pressure sensing pads are known for use in applications such as the detection of apnea or the like. They can be placed on the crib of an infant and are used to detect regular and periodic changes in pressure occasioned by the respiration and movement of the infant. If the infant should stop breathing, the failure to detect a change in pressure for a predetermined period of time provides an early indication of a possible alarm condition.

While most pressure sensing pads of the type known heretofore are capable of detecting the interruption of respiration, they are not suited for other uses. In particular, it is desirable to be able to measure the distribution of pressure on a surface. Information of this type would be invaluable to designers of sleep surfaces and furniture, for example. By knowing where the high-pressure points of a prone person are located, a bed can be designed which will more evenly distribute pressure and thereby diminish the occurrence of bedsores on patients who are confined for long periods of time. Similarly, the design of ergonomically efficient furniture is facilitated with such information.

Apnea monitoring pads are not suited for these types of applications because they are essentially qualitative measuring devices. In other words, they can detect if a pressure is being applied and whether it is changing, but they do not indicate how much pressure is being applied. Further they do not have the ability to provide any spatial resolution to the sensed pressure; they merely detect that it exists somewhere on the surface of the pad.

A significant problem that is encountered when attempts are made to provide spatial resolution of an applied pressure is the effect which various measuring points have on one another. For example, U.S. Pat. Nos. 4,134,063 and 4,437,138 disclose a pressure sensing pad that comprises a matrix of capacitive elements. Each capacitive element defines a measuring point. When a measurement is to be taken at a particular point, a voltage signal is applied to one terminal of the capacitor at that point, and a signal is obtained at the other terminal which is indicative of capacitance. Since the capacitance varies with the pressure on the pad at the location of the capacitor, the resulting signal provides pressure-related information.

However, since all of the capacitors are connected to each other in the matrix arrangement, errors can occur in the pressure measurement. More particularly, the signal obtained from one point will be influenced not only by the capacitance at that measuring point of interest but also by the capacitances of the surrounding points. Thus, changes in the surrounding pressures will be indicated in the measured signal and could result in erroneous readings.

The previously noted '063 patent contains a recognition of this problem. As a solution, it proposes that each of the input lines that supplies the voltage signal to the capacitors be connected to ground by a low-ohmic resistor. Apparently the resistor functions to shunt some of the error signal away from the output terminal of the capacitor of interest. While this approach attenuates the effect of the error on the measured signal, it would be preferable to eliminate or compensate the error signal to the greatest extent that can be practically obtained. For example, after supplying a voltage signal to one terminal of a selected capacitor of interest, capacitance is selectively measured at the other terminal of the capacitor by placing the latter terminal at an increased voltage potential. Such an increased voltage potential at the output terminal of the selected capacitor in the '063 patent is associated with the capacitor and diode utilized in the capacitance measuring voltage detection circuit $GS_k$.

Accordingly, it is a general object of the present invention to provide a novel capacitive system for measuring the spatial distribution of pressure.

It is a more specific object along these lines to provide such a system which eliminates the errors occasioned by interaction among commonly connected capacitors which affect the measured signal.

It is a further object of the invention to also eliminate the effects of noise from other sources which can introduce error into the pressure measurement.

It is a further object of the invention to provide a pad structure which does not generate noise that could interfere with external instrumentation used in the environment of a patient.

It is a further object of the invention to provide a novel pad structure for providing capacitive type measurements.

BRIEF STATEMENT OF THE INVENTION

In accordance with the present invention, these objects and their attendant advantages are provided in a pressure distribution measuring system that effectively places the output terminal of a selected capacitor at zero voltage during a capacitance measuring operation.

More specifically, the pressure distribution measuring system of the present invention includes a pad of insulating material disposed between two linear arrays of electrodes to form a matrix of capacitive nodes. All electrodes other than those associated with the selected node of interest are held at zero volts. In addition, a capacitance related output signal is obtained from the selected node of interest without permitting an error influencing voltage to be present on the electrode leading from the node (i.e., the output terminal of the selected capacitor). The absence of voltage on the electrode leading from the node in conjunction with the absence of voltage on the unselected electrodes prevents electronic interaction between nodes, i.e., inhibits the flow of current through commonly connected capacitors, and thereby isolates the measured signal from any changes in the capacitance of these other capacitors. The present invention is therefore also less susceptible to noise from other sources which could affect the pressure measurements. In addition, the pressure distribution system of the present invention does not create noise which could interfere with instrumentation in the environment of a patient.

In a preferred embodiment of the present invention, the absence of an error influencing voltage at the electrode leading from a selected node is achieved by using a current-sensing amplifier to measure capacitance. To maintain a zero voltage condition on this electrode, the input impedance of the current-sensing amplifier is effectively placed at or near zero.

As a further feature of the invention, a novel pad construction is proposed which increases the amplitude of the measured signal, isolates the measured signal from the ambient environment, and reduces the susceptibility of the measuring process to errors caused by wrinkling of the pad as a person lies on it, or the like.

The manner in which these concepts are implemented is explained in greater detail hereinafter with reference to a preferred embodiment of the invention illustrated in the accompanying drawings.

DESCRIPTION OF THE ILLUSTRATED EMBODIMENT

In the following description, particular reference is made to the use of the invention in the context of measuring the distribution of the pressure exerted by a person lying on a mattress. It will be appreciated, however, that the practical applications of the invention extend to many other areas in which knowledge of actual pressure and/or its distribution would be useful.

Figure 1:
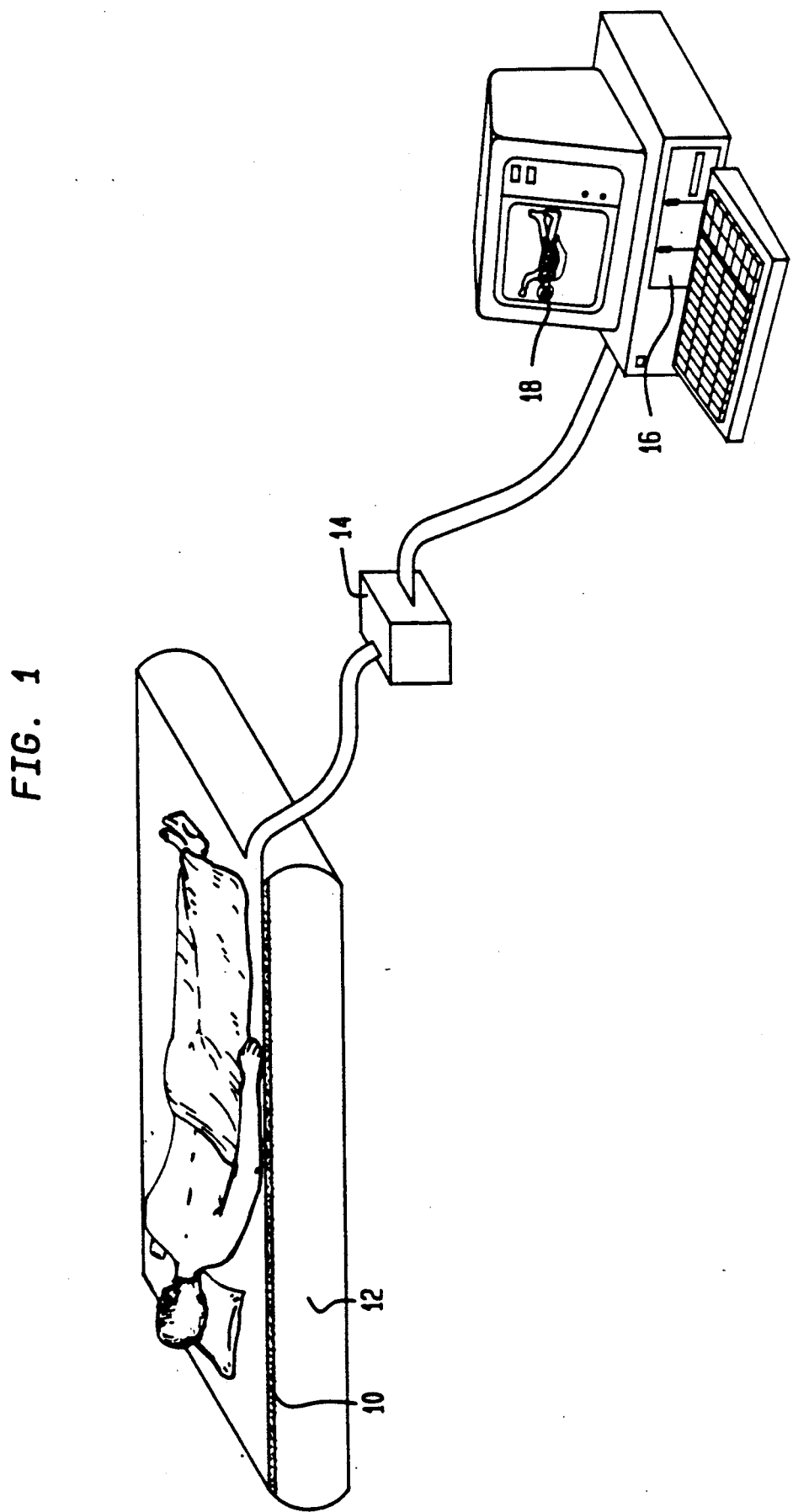
FIG. 1 is a general perspective view of the overall measuring system as it might be used to determine the distribution of pressure of a person lying on a mattress.

Referring to FIG. 1, the pressure measuring system of the present invention is comprised of three main components, a pressure sensitive pad 10 that can be placed on top of a mattress 12 to measure the weight distribution of a person lying on it, an interface unit 14 for supplying electrical driving signals to the pad and receiving pressure sensitive output signals from it, and a signal processing device, for example a microcomputer 16 with an associated graphic display monitor 18, for controlling the interface unit and processing the output signals from the pad. In operation, the pad 10 produces output signals that are indicative of the pressure that is sensed at each of a multiplicity of points over its surface area. The computer 16 receives these signals, by way of the interface unit, and causes a display to be generated which illustrates the distribution of the weight of the patient over the area of the pad.

Figure 2:
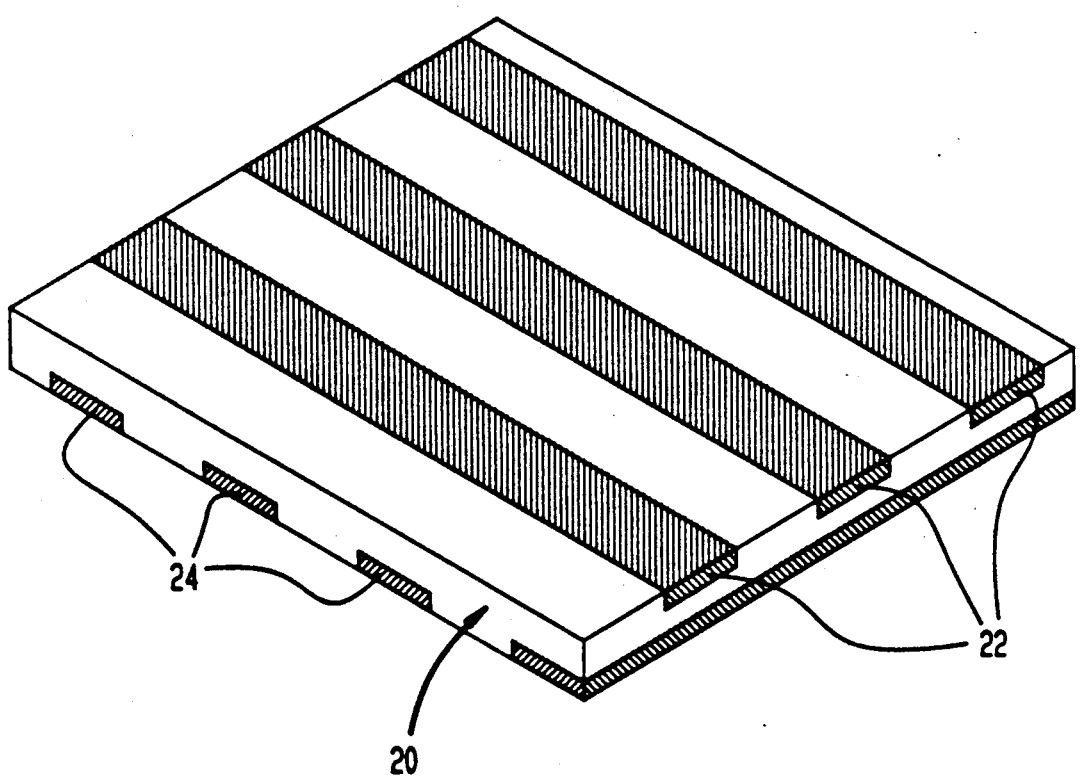
FIG. 2 is a perspective view illustrating the general construction of a pressure-responsive capacitive measuring pad.

The basic construction of the pad 10 is illustrated in FIG. 2. It comprises a compressible dielectric layer 20 having two linear arrays of electrodes 22 and 24 respectively disposed on opposite sides thereof. The dielectric layer can be an open cell foam having a nominal, i.e., unloaded, thickness of about 5 mm. One of the arrays 22 comprises a series of parallel linear electrodes that are oriented in one direction. The other array 24 similarly comprises a series of parallel linear electrodes which are oriented in a direction that is perpendicular to the orientation of the electrodes in the first array 22. Each intersection of an electrode of one array with an electrode of the other array defines a measuring node. Since the thickness of the dielectric layer 20 between the intersecting electrodes varies with applied pressure, its capacitance also varies. Thus the capacitance at each node provides an indication of the pressure applied at that point.

Figure 3:
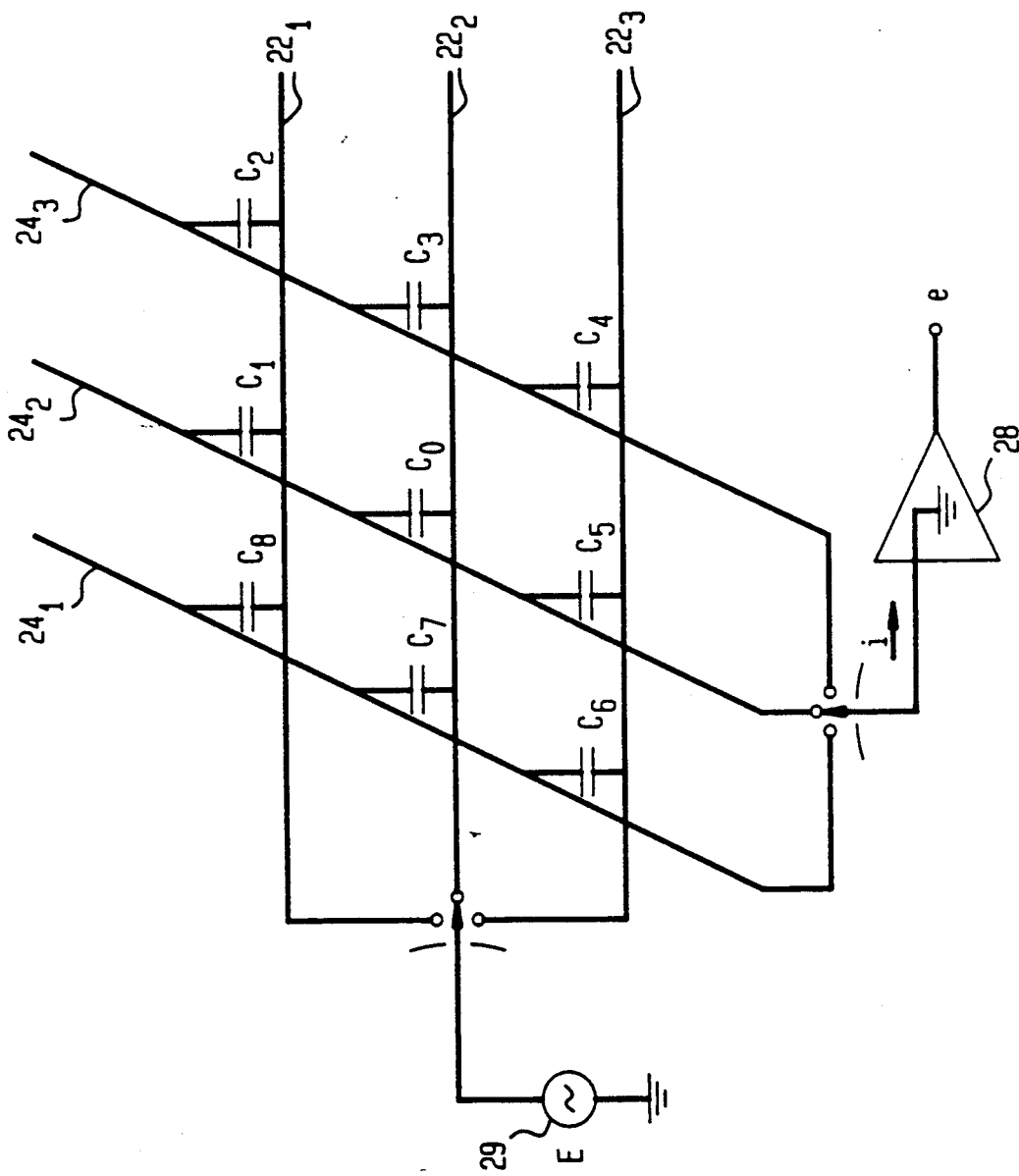
FIG. 3 is a schematic diagram of the capacitive circuit formed by the pad of FIG. 2.

The equivalent circuit that is formed by the structure of FIG. 2 is illustrated in FIG. 3. The measuring nodes are represented by capacitors $C_0$–$C_8$ that are disposed in a matrix arrangement. All of the capacitors in a row of the matrix are connected in common to one of the electrodes 22 of the first array, and all of the capacitors in a column of the matrix are connected in common to one of the electrodes 24 of the other array. When it is desired to measure the capacitance of a particular node, a driving signal having a known voltage E is applied to the electrode 22 associated with the row in which the node is located. Referring to the specific example illustrated in FIG. 3, if it is desired to measure the capacitance of capacitor $C_0$, the driving signal is applied to the middle electrode, $22_2$. The current from the measured capacitance is sensed via the electrode, $24_2$, associated with the column in which the capacitor is located. This electrode is connected to a current-sensing amplifier 28 with low input impedance. Ideally, the input impedance of the current-sensing amplifier 28 is zero; practically, it is sufficient for the input impedance of the current-sensing amplifier to be small with respect to the impedances of the capacitances formed by the electrode arrays. The current-sensing amplifier 28 produces an output signal related to the capacitance of the node $C_0$ according to the following relationship:

$$e = sAC_0E$$

where:

e is the output voltage from amplifier 28, s is a sinor,

E is the voltage that is applied as a driving signal, $C_0$ is the variable capacitance at the measuring node, A is the current-to-voltage gain of the amplifier 28.

The capacitance at the node is determined by the thickness of the dielectric layer at that point, which is, in turn, a function of pressure. A higher capacitance represents a thinner dielectric layer and hence a greater applied pressure. The transfer function of the system can be defined in terms of pressure as follows:

$$\frac{e}{E} = K_o \frac{1 + K_1 p}{1 + K_2 p}$$

where: $K_0$, $K_1$ and $K_2$ are constants related to the stress-strain characteristics of the dielectric layer, the dielectric constant of the dielectric layer, the area of a node, and other circuit parameters; and, p is pressure applied at the node.

Thus, the signal that is obtained on an electrode 24 can be quantified in terms of applied pressure as follows:

$$p = \frac{K_o^{E-\epsilon}}{\epsilon K_2 - K_o K_1 E}$$

One factor that needs to be addressed when pressure is to be quantified is the interaction among the nodes. In particular, the signal which is sensed on the electrode $24_2$ will not be limited to only the capacitance at the node $C_0$. Referring to FIG. 3, the primary path from the driving electrode $22_2$ to the sensing electrode $24_2$ is through the capacitor $C_0$. However, the driving signal can also follow a parallel path comprising capacitor $C_3$, electrode $24_3$, capacitor $C_2$, electrode $22_1$ and capacitor $C_1$. Thus, any change in the capacitance of capacitors $C_1$, $C_2$ or $C_3$ affects the measurement that is obtained on the electrode $24_2$. Similarly, since the driving signal can follow other parallel paths formed by other sets of surrounding capacitors, changes in their capacitance will also affect the measured signal.

Figure 4:
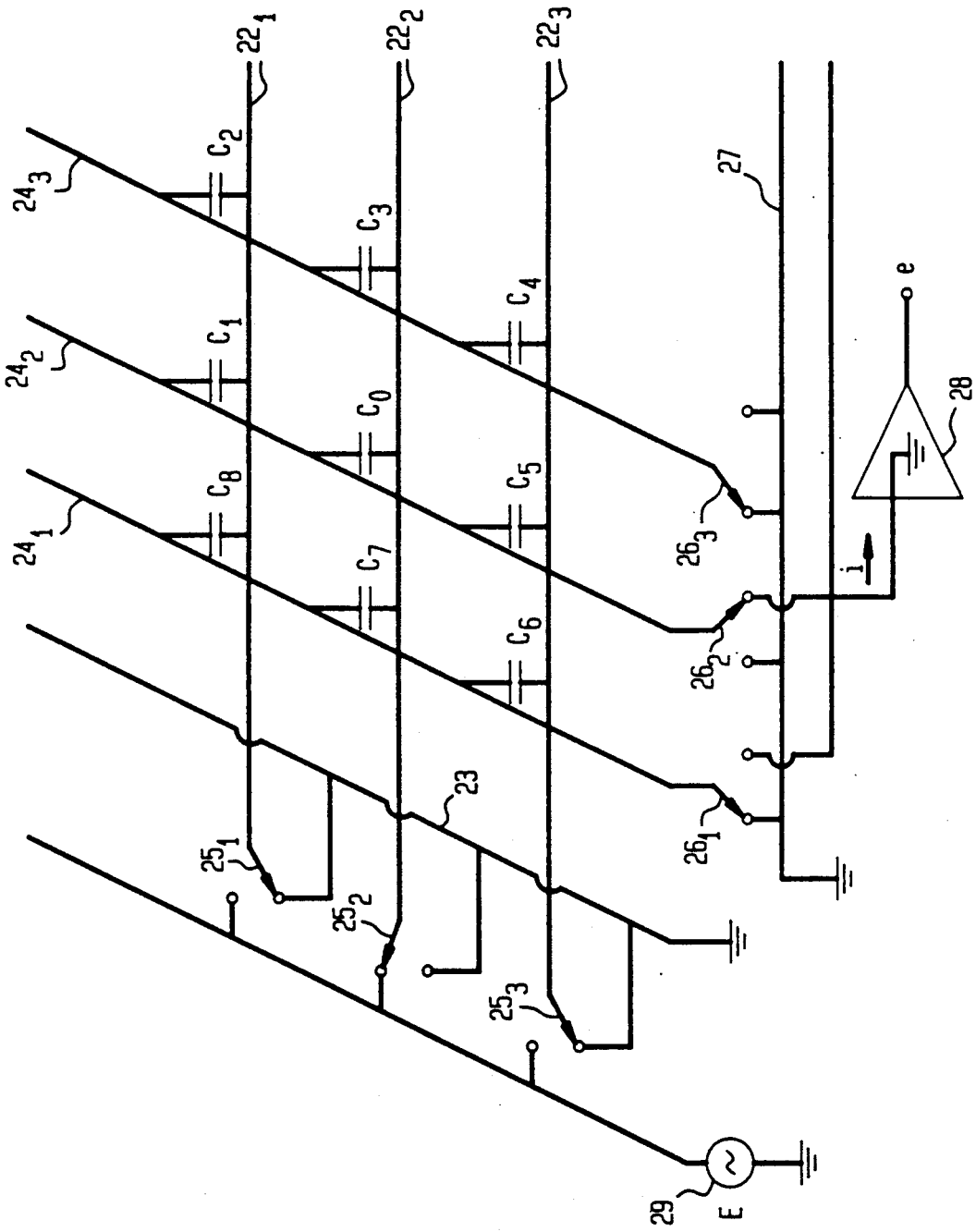
FIG. 4 is a schematic diagram of the capacitive circuit formed by the pad of FIG. 2, and illustrates the use of multiple double-throw switches to eliminate electronic interaction between unselected nodes and the selected node.

In accordance with the present invention, the effects of the surrounding capacitors on the measured signal are eliminated by connecting all of the electrodes, other than the one associated with the row of interest, to ground and by using a current-sensing amplifier having a low input impedance. Referring to FIG. 4, the measuring nodes are represented by capacitors $C_0$–$C_8$ that are disposed in a matrix arrangement, in a manner similar to FIG. 3. Unlike the arrangement of FIG. 3, however, each of the electrodes 22 of the first array is normally connected to a zero voltage, or ground potential, line 23 by means of respective double pole switches 25. Likewise, each of the electrodes 24 in the second array is normally connected to a ground potential line 27 by means of respective double pole switches 26.

When it is desired to measure the capacitance of capacitor $C_0$, the driving signal is applied to the middle electrode, $22_2$, by activating the double-pole switch $25_2$. The measured capacitance is sensed on the electrode, $24_2$, associated with the column in which the capacitor is located. This electrode is connected to the current-sensing amplifier 28 with low input impedance by activating the double-pole switch $26_2$. All other row switches, 25, and column switches, 26, are left in the inactive state so that their electrodes, 22 and 24, respectively, are connected to ground. An important consequence of this arrangement is that only one electrode, the row (drive) electrode connected to the voltage source and corresponding to the selected node capacitance, has an impressed voltage. All other electrodes in the entire array, including the selected column electrode, $24_2$, are at zero volts. For example, as shown in FIG. 4, the drive (row) electrodes $22_1$ and $22_3$, associated with unselected capacitors $C_1$, $C_2$, $C_4$, $C_5$, $C_6$ and $C_8$ are connected to ground by their respective switches, $25_1$ and $25_3$. Similarly, the sense (column) electrodes, associated with unselected capacitors $C_2$, $C_3$, $C_4$, $C_6$, $C_7$ and $C_8$ are connected to ground by their respective switches, $26_1$ and $26_3$.

Ideally, the voltage of the selected column electrode, $24_2$, is also zero. If, however, the impedance of the current-sensing amplifier is permitted to have some relatively small impedance as mentioned above, the voltage of the selected column electrode, $24_2$, will be practically zero. "Practically" in this context is taken to mean close enough to zero so that the selected column electrode can be considered to be connected to ground and so that any current generated in the unselected capacitors of the electrode $24_2$ will remain within acceptable limits which do not significantly affect the capacitance of the selected node. Consequently, a change in capacitance of a node with an electrode common to the selected node introduces no error in the output signal. A change in capacitance of a node in the same row as the selected node, for example, at the nodes that correspond to capacitors $C_7$ and $C_3$ merely changes the current that must be supplied by the voltage source, E. A change in the capacitance of a node in the same column as the selected node, for example, at the nodes that correspond to capacitors $C_1$ and $C_5$ introduces no error because both of the electrodes of these capacitors are at zero volts, and hence, no current flows through them. An important additional consequence of the fact that no voltage exists on the selected column electrode is that possible error due to any stray capacitance, for example the capacitance of the cable connecting the interface to the pressure-sensitive mat, is eliminated.

Figure 5:
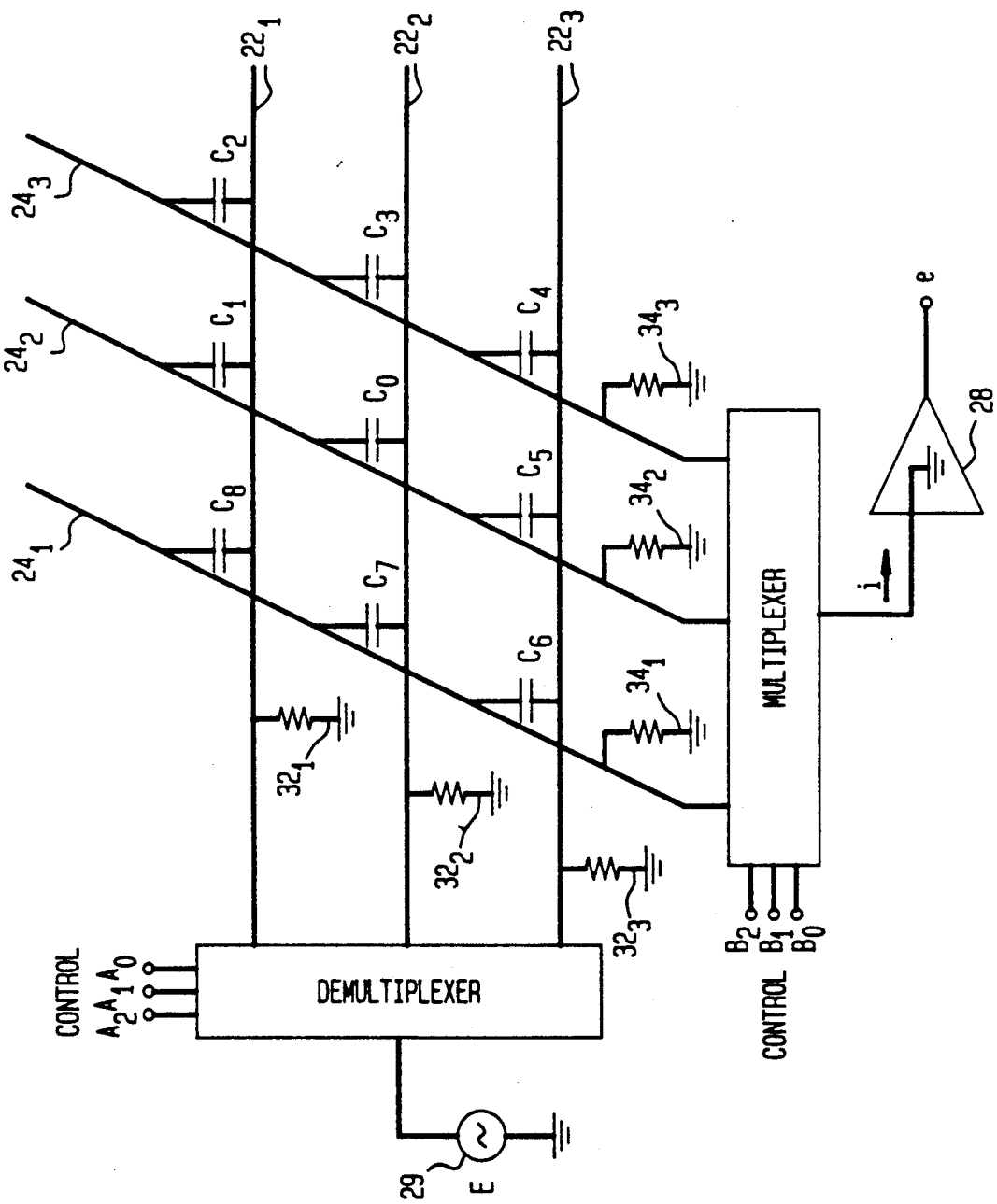
FIG. 5 is a schematic diagram of the capacitive circuit formed by the pad of FIG. 2, and illustrates the use of multiplexer/demultiplexer switches to attenuate electronic interaction between unselected nodes and the selected node.

Similar isolation between nodes can be achieved by the use of terminating resistors and multiplexer/demultiplexer switches, as shown in the embodiment of FIG. 5. In this embodiment each of the drive electrodes 22 in the first array is connected to ground through a respective terminating resistor 32. Similarly, each of the sense electrodes 24 in the second array is connected to ground through a respective terminating resistor 34. The resistance of the resistors, $R_{32}$, should be much smaller than the impedance of the nodes, but must be large enough so as not to unduly burden the voltage source, E. The values for the resistors $R_{34}$ are preferably chosen so that their impedance, in combination with the impedances of the capacitances at the measuring modes, render the input impedance of the current-sensing amplifier 28 to be relatively small. As a practical matter, it may also be necessary to consider the resistance of the multiplexer switches when selecting the appropriate value of resistance for the resistors, $R_{32}$ and $R_{34}$.

Figures 6, 6A:
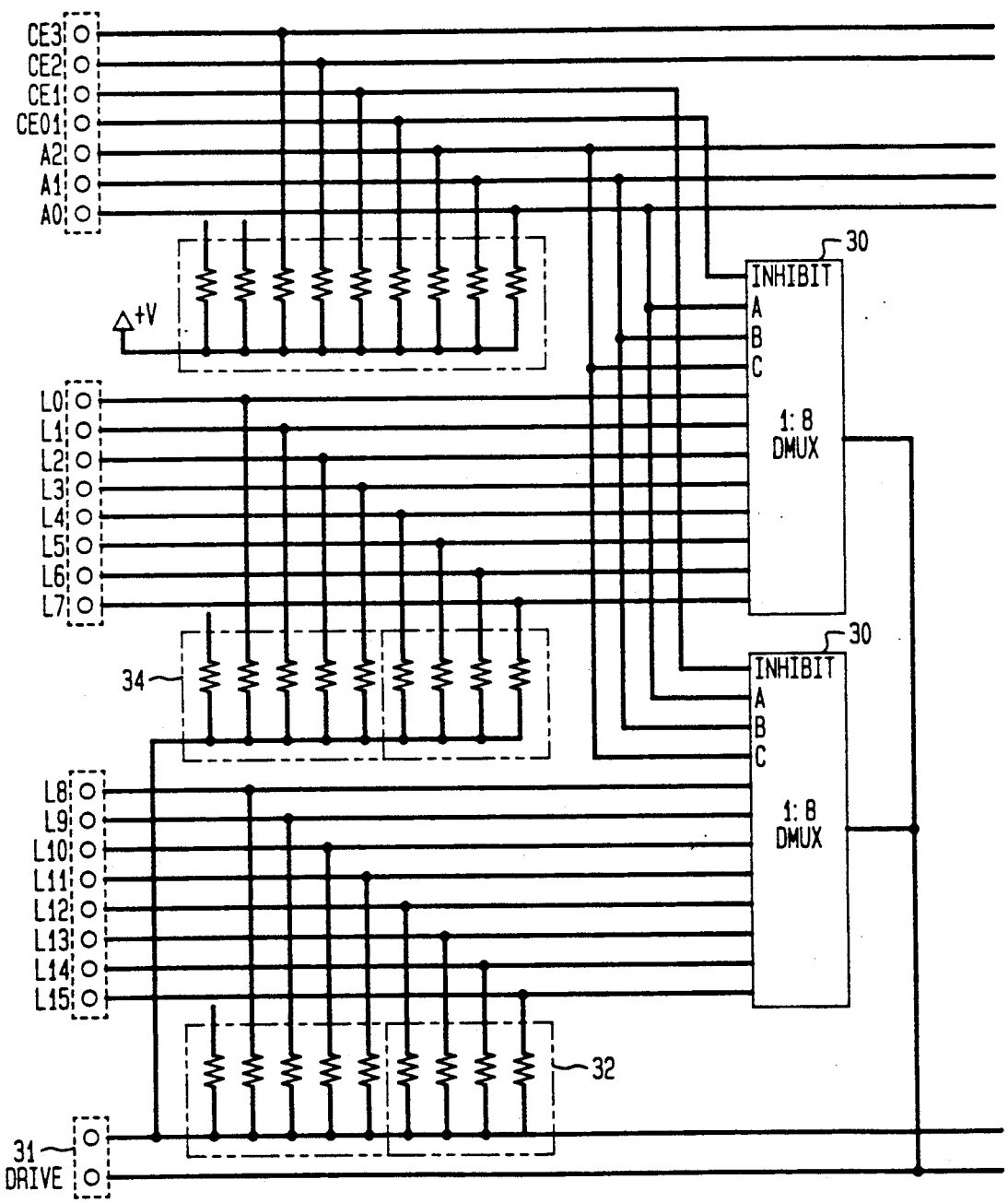
FIG. 6 is a schematic and block diagram of the demultiplexing circuit for supplying the driving signal to the arrays of the pad.
Figure 6B:
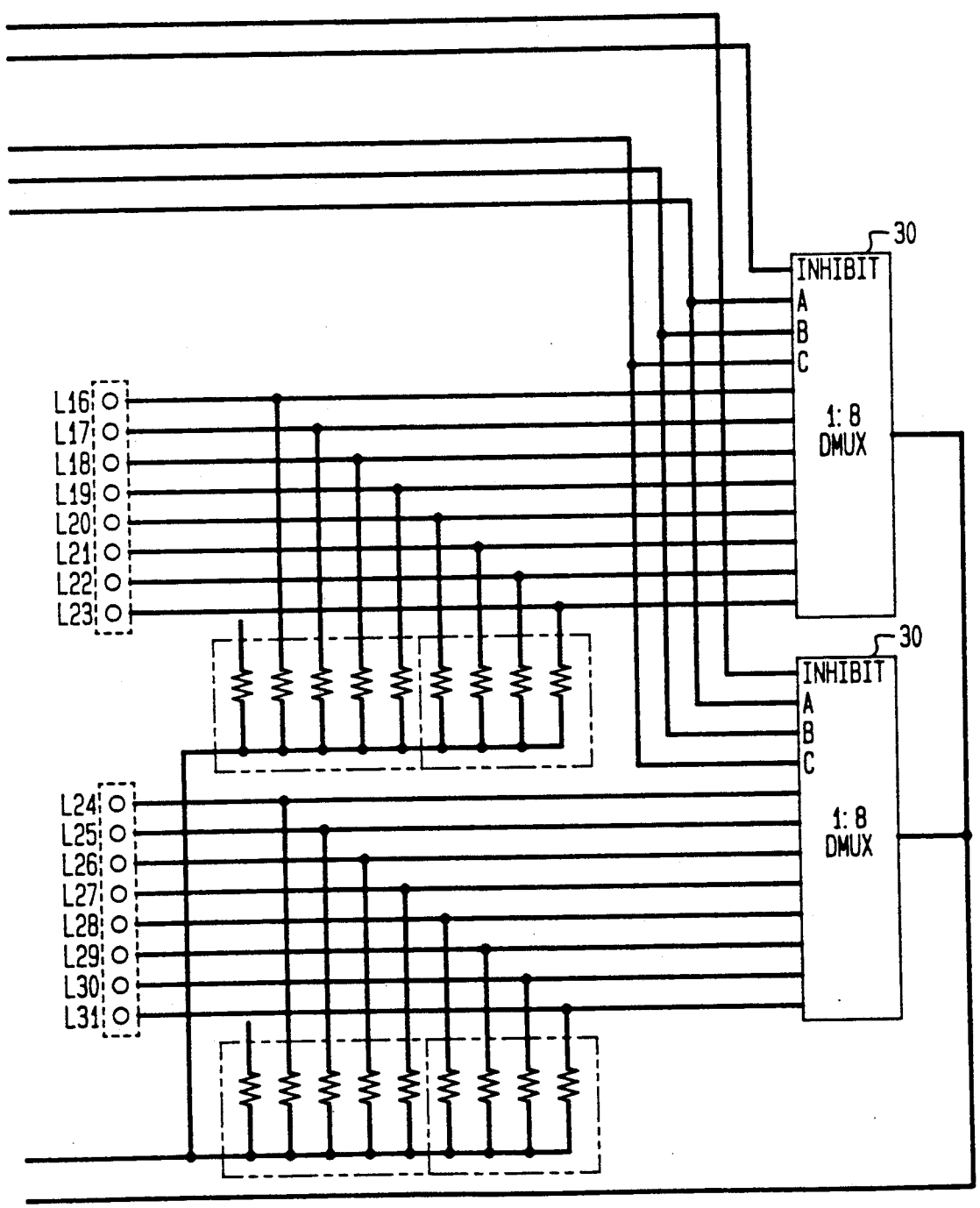

A circuit for implementing the embodiment of FIG. 5 is illustrated in FIG. 6. This circuit is contained within the interface unit 14. The illustrated embodiment pertains to a pad which might be of a suitable size for use on a full-sized mattress. Such a pad can have 32 electrodes in the driving array and 64 electrodes in the sensing array to form a matrix of 2048 measuring points. The driving electrodes are respectively labelled L0–L31 in FIG. 6. The electrodes are grouped into four sets of eight electrodes each, and each set is respectively connected to the eight output lines of a 1:8 demultiplexer (DMUX) 30. To select one of the drive lines, the particular DMUX to which that line is connected is activated by means of a chip enable signal CE0–CE3. Address signals A0–A2 identify the particular one of the eight output lines of the DMUX that is to be driven. In response to these signals the activated DMUX connects a input driving voltage DRIVE to the identified line. For example, the driving signal can be an 8-volt A.C. signal having a frequency of about 20 KHz.

Each of the drive lines is connected to a ground terminal 31 by means of an electrode-terminating resistor 32. The resistors 32 function to shunt error currents to ground, yet isolate the driven electrode from ground so that it will be at the proper voltage. Preferably, the resistors have a value of around 10K ohms each to provide this function. If their resistance is too low, e.g., 100 ohms, the driving signal will be shorted and the output will be attenuated. On the other hand, if the resistance is too large, e.g., 500K ohms, a voltage will appear on the unselected electrodes, and pressures applied at nodes other than the selected node will cause an error signal.

Figure 7:
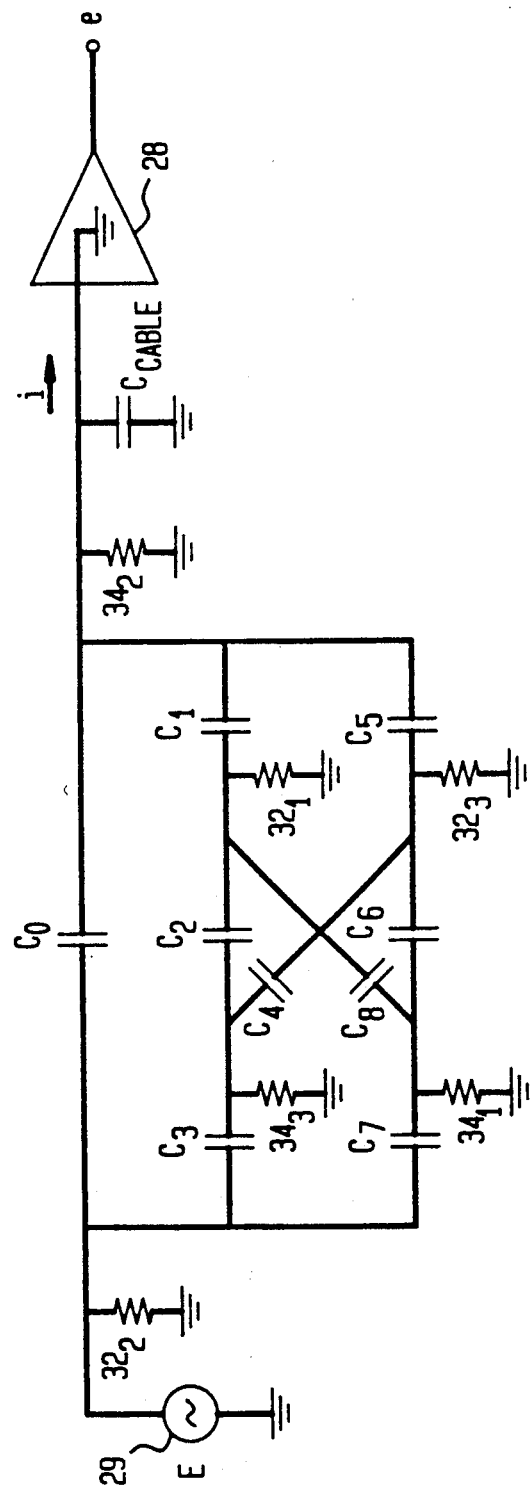
FIG. 7 is a schematic diagram of the equivalent circuit for a selected node and its eight nearest neighbors.

An equivalent circuit can be drawn to facilitate analysis of node interactions for the circuit shown in FIG. 5. The equivalent circuit that is formed when the node with capacitance $C_0$ is selected is shown in FIG. 7. The capacitors $C_3$ and $C_7$, which share the selected drive line with $C_0$, provide a parallel current path to the input terminal of the current-sensing amplifier. However, the current pathway includes two shunt pathways to ground via the electrode-terminating resistors 32.

The equivalent circuit shown in FIG. 7, which serves to illustrate the internode interaction problem for a 9-node pad, can be extended to a full-sized pad, for example, one containing 2048 nodes. The error current, $i_{err}$, presented to the input of the current-sensing amplifier is approximately:

$$i_{err} = s^3 C_x C_r R_x R_r E$$

where:

$C_x$ is the sum of the capacitances of the unselected sensing columns, $C_r$ is the sum of the capacitances of the unselected drive rows, $R_x$ is the electrode-terminating resistance divided by the number of unselected columns, $R_r$ is the electrode-terminating resistance divided by the number of unselected rows, s is a sinor, and E is the voltage that is applied as a driving signal.

The error current can be reduced to a negligible value by selecting the electrode terminating resistance much smaller than the reactance of a node. For example, in the preferred embodiment, selecting the electrode-terminating resistance to be 10K reduces the error current by more than 100 db with respect to the current from the selected node, and hence, reduces the error caused by internode interaction to less than 0.001%.

In operation, the computer sends control signals to the interface unit to sequentially scan each of the measuring nodes. This scanning is carried out through the coordinated addressing of the driving electrode DMUX 30 and a similar multiplexer (not shown) connected to the sensing electrode, as disclosed for example in U.S. Pat. No. 4,134,063. The computer calculates the absolute pressure at each measured node from the sensed signals in accordance with the relationship defined previously.

The screen of the display monitor 16 is divided into a matrix of cells which correspond to the nodes of the pad. The range of measured pressures can be divided into units that are correlated with individual colors in a color spectrum. The pressure that is measured at each node can thus cause a particular color to be displayed within its associated cell on the screen to provide an easily readable map of pressure distribution in which pressure gradients are indicated by a change in color from one cell to the next.

As a further feature, the weight of the patient can be determined and indicated on the display by summing the pressure that is measured at each node.

Figure 8:
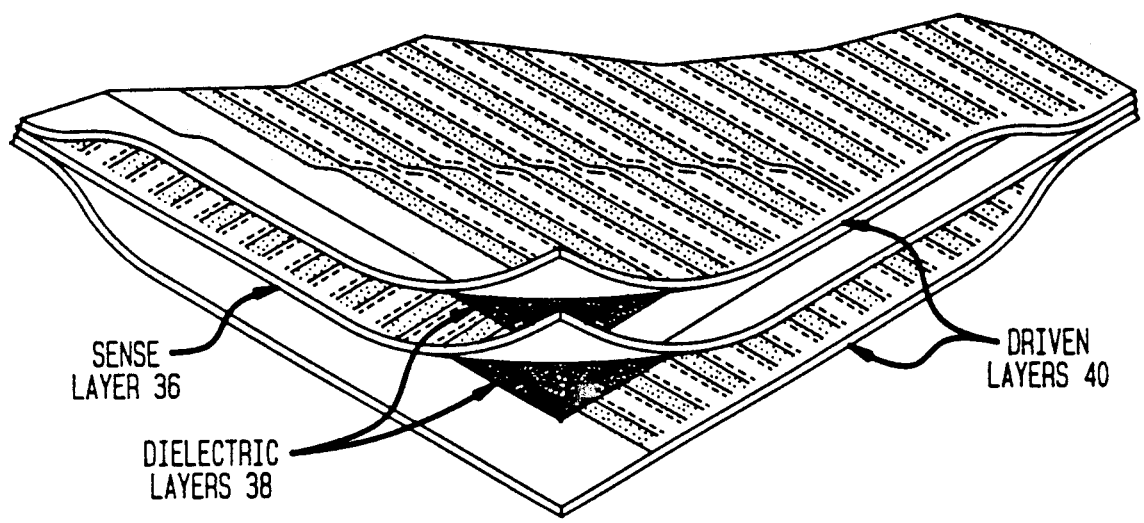
FIG. 8 is a perspective view of a preferred embodiment of the pad.
Figure 9:
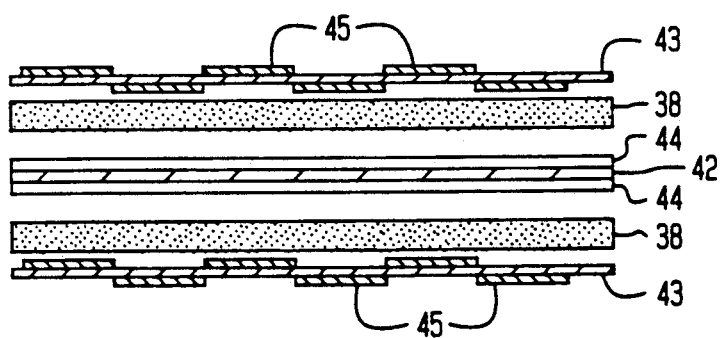
FIG. 9 side view of the pad of FIG. 8.

A preferred form of construction for the pad 10 is illustrated in FIGS. 8 and 9. This pad essentially comprises a symmetric integration of two pads of the general type depicted in FIG. 2. A central sensing electrode layer 36 has insulating foam layers 38 disposed on both sides of it. Driving electrode layers 40 are located on the exterior of each of the foam layers. Each electrode layer 36, 40 is comprised of a support material 42, 43, preferably a non-conductive fabric, that has conductive linear electrodes 44, 45 attached to it. Each electrode preferably comprises a strip of conductive fabric, e.g., a nylon that is bonded with a metal such as silver. As best illustrated in FIG. 9, the conductive electrode strips are arranged on alternate sides of the fabric. This arrangement inhibits adjacent electrodes in an array from being shorted due to small wrinkles in the fabric.

The electrodes in the two outer driving layers are aligned with one another, and each pair of aligned electrodes are electrically connected in common with one another. Accordingly, each measuring node is defined by the area of the intersection of a sensing electrode 44 with an aligned pair of driving electrodes 45. This arrangement provides a number of advantages. For example, the capacitance at each node comprises the sum of two capacitors connected in parallel, i.e., one capacitor formed between the sensing electrode layer 36 and the upper driving electrode layer and another capacitor formed between the sensing layer and the lower driving electrode layer. Thus, the signal that is measured is effectively doubled over that which is obtained with a pad having a single insulating layer, and hence easier to read. If the two electrodes in the upper and lower driving layers are not perfectly aligned, the measured signal will not be adversely affected. Rather, any misalignment will merely result in a loss of spatial resolution of the area of the node.

As another advantage, the driving electrode layers that are symmetrically disposed on opposite sides of the sensing layer form electrostatic planes which shield the sensing electrodes from both the patient and the mattress. Thus, the measured signal is less likely to be disturbed by outside influences.

To maintain symmetry and ensure that each capacitive node has the same construction, the over-and-under relationship of the upper and lower driving electrodes is preserved relative to one another. Referring to FIG. 9, it can be seen that if an upper driving electrode 45 is disposed on the exterior side of its support 43, the corresponding lower electrode is located on the interior side of its support, and vice versa. Thus, each pair of parallel connected capacitors at a node will have one capacitor which includes the support fabric 43 between the driving and sensing electrode, and another capacitor which does not include the fabric. To the extent the support fabric has an influence on the capacitance of a node, that effect will be the same for all nodes.

The material that is selected for the dielectric layers 38 should have as little hysteresis as possible in its stress-strain characteristics over the pressure range of interest. If the hysteresis is too large, a patient could pre-load the pad as he gets on the mattress, and hence provide erroneous readings. In addition, the material should exhibit negligible creep and have no "memory", i.e., acquire no permanent compression under prolonged loading conditions. If a synthetic foam is used as the dielectric material, a charcoal filled foam provides good results. One example of a suitable charcoal-filled foam is Type SBR foam manufactured by Ludlow. Natural Lutex foam also serves well as a compressible dielectric.

An even more ideal material in this regard is air, since it exhibits very little hysteresis. In the implementation of the invention, individual pockets of air can be confined between two sheets of plastic that are bonded to one another in a matrix pattern. A dielectric layer of this type would have an appearance similar to the "bubble pack" type of material that is used to protect fragile items during packing and shipping. Each pocket of air would define one measuring node, and the electrodes can be easily deposited on the plastic confining layers.

From the foregoing it will be appreciated that the present invention provides a capacitance measuring system that enables the distribution of pressure over a surface to be quantitatively measured and displayed. As noted previously, the information that is provided by the system is useful in the design of sleep surfaces and other furniture, and possibly even clothing. In addition to providing design information, the measuring system can be used in other applications. For example, it can be used to monitor apnea or to detect the exit of a patient from a bed. It might even be used as part of a dynamic feedback system in which the contour of a bed is automatically adjusted in response to movements of the patient to accommodate various reclining positions.

It will therefore be appreciated by those of ordinary skill in the art that the present invention can be embodied in other specific forms without departing from the spirit or essential characteristics thereof. The presently disclosed embodiment is considered in all respects to be illustrative and not restrictive. The scope of the invention is indicated by the appended claims rather than the foregoing description, and all changes that come within the meaning and range of equivalents thereof are intended to be embraced therein.

What is claimed is:

1. A system for monitoring the distribution of forces on a surface, comprising:
   a pad having first and second arrays of linear electrodes respectively disposed on opposite sides of a sheet of compressible insulating material, the electrodes of said first array being oriented in a direction other than the direction of orientation of the electrodes of said second array to thereby form a matrix of nodes each of which is located at an intersection of an electrode of one array with an electrode of the other array and which has a capacitance that varies in accordance with compression of the insulating material at said intersection;
   means for sequentially selecting the electrodes of said first array and applying an electrical driving signal to the selected electrode;
   means for sequentially selecting the electrodes of said second array;
   means for sensing an electrical current of the selected electrode of said second array to thereby measure the capacitance of the associated node at the intersection of the two selected electrodes;
   means for connecting each of the non-selected electrodes of said first array to a reference voltage to thereby isolate said sensed node from the effects of changes in capacitance of nodes other than said sensed node whose capacitance is being measured; and
   means for connecting each of the electrodes of said second array, including the selected electrode of said second array, to said reference voltage to thereby further isolate said sensed node from effects of changes in capacitance of nodes other than said sensed node whose capacitance is being measured and to reduce the effects of cable capacitance on the current from said sensed node.

2. The system of claim 1, further including means for displaying a distribution of forces on said pad as a matrix of cells with each cell depicting the relative capacitance of an associated node on said pad.

3. The system of claim 2, wherein the capacitances of said nodes are in a range which is associated with a spectrum of colors and pressure gradients are represented on said display means by a change in color from one cell to another.

4. The system of claim 1, further including means for determining an absolute pressure on the pad at each node thereof in response to the measured capacitance of the node.

5. The system of claim 4, further including means for summing the pressures at all of the nodes to thereby determine the weight of an object on the pad.

6. The system of claim 1, wherein said means for sensing includes an amplifier which receives said electrical current of said selected electrode of said second array as an input signal and which exhibits an input impedance much smaller than the impedance of said nodes.

7. The system of claim 1, wherein each of the electrodes of said first array and said second array are connected to the reference voltage via resistors.

8. The system of claim 7, wherein said means for sensing includes an amplifier which receives said electrical current of said selected electrode of said second array as an input signal and which exhibits an input impedance much smaller than the impedance of said nodes and said resistors connecting the electrodes of said second array to said reference voltage.

9. The system of claim 7, wherein the resistance of said resistors connecting each of the electrodes of said first array to the reference voltage is much smaller than the impedance of each node.

10. The system of claim 1, wherein said pad further includes a third array of linear electrodes, the electrodes in said third array being oriented parallel to and in alignment with the electrodes of said first array and being disposed on a side of said second array opposite said first array, and also including a second sheet of compressible insulating material interposed between said second and third arrays of electrodes, the electrodes of said third array being sequentially selected in correspondence with those of said first array to thereby effectively form two capacitors connected in parallel with one another at each node.

11. The system of claim 10, wherein each array of linear electrodes comprises conductive strips disposed on a substrate, and wherein the conductive strips of at least said first and third arrays are disposed on opposite sides of their respective substrates in an alternating fashion.

12. The system of claim 11, wherein each aligned pair of strips in the first and third electrodes are disposed on the same side of their respective substrates so that, at each node, one of the strips of the pair is disposed on the side of its substrate which is away from said second array and the other strip of the pair is disposed on the side of its substrate which is closest to said second array.

13. The system of claim 1, wherein said reference voltage is ground.

14. Apparatus for sensing the distribution of pressure on a surface, comprising:
    first and second sheets of compressible insulating material;
    a first array of linear electrodes interposed between said sheets of material and being oriented in a first direction;
    a second array of linear electrodes disposed on a side of said first sheet that is opposite said first array and being oriented in a second direction which intersects said first direction;
    a third array of linear electrodes disposed on a side of said second sheet that is opposite said first array, the electrodes of said third array being parallel to and in substantial alignment with the electrodes of said second array, each electrode in said third array being electrically connected to a corresponding aligned electrode in said second array to thereby effectively form two capacitors connected in parallel at each node formed at the intersection of an electrode in said first array with an aligned pair of electrodes in said second and third arrays; and
    means for sensing an electrical current of a selected electrode of said first array to thereby measure capacitance of an associated node, said electrodes of said first array, including said selected electrode being connected to a common reference voltage.

15. The apparatus of claim 14, wherein the electrodes of said second and third arrays are oriented perpendicular to the electrodes of said first array.

16. The apparatus of claim 14, wherein said insulating material comprises a foam.

17. The apparatus of claim 14, wherein each of said sheets of insulating material comprises two layers of material which are joined to one another in a manner which forms enclosing cells of air between them, each cell being associated with one of said nodes.

18. A system for monitoring the distribution of forces on a surface, comprising:
    a pad having first and second arrays of electrodes and insulating material disposed between said first and second arrays to form a matrix of capacitive nodes each of which has a capacitance that varies in accordance with the degree of pressure on the pad at the location of the node;
    means for scanning the electrodes of said first and second arrays to thereby successively address nodes in said matrix;
    means for measuring the capacitance of an addressed node by sensing current of a scanned electrode of said second array; and
    means for connecting each electrode of said second array to a reference potential for the driving signal to thereby render all electrodes of said second array at substantially zero volts to thereby isolate the measured capacitance from the effects of changes in capacitance of nodes other than the addressed node whose capacitance is being measured.

19. The system of claim 18, further including means for connecting each electrode of said first array which is not associated with said addressed node to said reference potential to thereby render all electrodes of said first array except for the addressed node at zero volts.

20. The system of claim 19, wherein said measuring means comprises means for applying a predetermined voltage to a selected electrode of said first array, means for measuring the current from a selected electrode of said second array, and an amplifier having an input impedance that is negligible compared to any of the impedances formed by said arrays such that the selected electrode of said second array is practically at zero volts.

21. The system of claim 20, wherein said reference potential is ground.

* * * * *